United States Patent [19]

Sotoguchi et al.

[11] Patent Number: 5,945,559
[45] Date of Patent: Aug. 31, 1999

[54] PROCESS FOR PRODUCING 3-OXOCARBOXYLIC ACID ESTERS

[75] Inventors: Tsukasa Sotoguchi; Yoshifumi Yuasa; Akio Tachikawa; Shunichi Harada, all of Kanagawa, Japan

[73] Assignee: Takasago International Corporation, Tokyo, Japan

[21] Appl. No.: 08/862,263

[22] Filed: May 23, 1997

[30] Foreign Application Priority Data

May 24, 1996 [JP] Japan .................................. 8-151896
Mar. 31, 1997 [JP] Japan .................................. 9-94338

[51] Int. Cl.$^6$ ............................ C07C 69/66; C07C 69/76
[52] U.S. Cl. .............................................. 560/174; 560/51
[58] Field of Search ........................ 560/174, 51

[56] References Cited

U.S. PATENT DOCUMENTS

| 4,820,745 | 4/1989 | Müller et al. | .............................. 522/90 |
| 4,822,829 | 4/1989 | Müller et al. | .............................. 522/90 |
| 5,144,057 | 9/1992 | Eyer | ........................................ 560/51 |
| 5,194,671 | 3/1993 | Meier | ...................................... 560/126 |

FOREIGN PATENT DOCUMENTS 6-145633  5/1994  Japan .
WO9628519  9/1996  WIPO .

OTHER PUBLICATIONS

Chem. Rev. 1995, 95, 1065–114.
Helvetica Chimica Acta. Volummen XXXV, Fasciculus VII (1952)—No. 284. p. 2280.

*Primary Examiner*—Paul J. Killos
*Attorney, Agent, or Firm*—Sughrue, Mion, Zinn, Macpeak & Seas, PLLC

[57] ABSTRACT

A novel process for producing 3-oxocarboxylic acid esters, which are useful as intermediates in the synthesis of ceramides to be used as a humectant, biodegradable polymers, drugs, etc., at a high purity and a high yield without requiring any troublesome procedure, is disclosed. The process comprises reacting an acetoacetic ester with a calcium compound, a barium compound or a strontium compound in the presence of an organic solvent at a temperature of 10 to 120° C., further reacting the obtained product with a carboxylic acid chloride to thereby acylate it, and then adding thereto an alcohol in an amount 1 to 5 times by mol as much as the calcium compound, barium compound or strontium compound to thereby deacetylate the same.

11 Claims, No Drawings

PROCESS FOR PRODUCING 3-OXOCARBOXYLIC ACID ESTERS

FIELD OF THE INVENTION

This invention relates to a process for producing 3-oxocarboxylic acid esters which are useful as intermediates in the synthesis of ceramides to be used as a humectant, biodegradable polymers, drugs, etc.

BACKGROUND OF THE INVENTION

There have been reported a number of processes for producing 3-oxocarboxylic acid esters which are called β-ketoesters in general.

For example, Chem. Rev., 95, 1065–1114 (1995) discloses a process for producing β-ketoesters which comprises condensing a carboxylic acid chloride with a malonic acid ester or an acetoacetic ester in the presence of a base followed by decarboxylation or deacetylation. As the base component to be employed in this process, use is made of, for example, sodium hydride, sodium amide or alkali metal alcoholates.

As improvements in the base component in the reaction for condensing an acetoacetic ester with a carboxylic acid chloride, further, it is suggested to use magnesium alcoholates [Helv. Chem. Acta., 35, 2280 (1952)] or calcium compounds (U.S. Pat. No. 5,194,671).

Furthermore, U.S. Pat. No. 5,144,057 and JP-A-57-70837 each discloses a process for producing β-ketoesters which comprises reacting a magnesium complex or a calcium complex of an acetoacetic ester with a carboxylic acid chloride (The term "JP-A" as used herein means an "unexamined published Japanese patent application").

However these processes with the use of sodium hydride, sodium amide, alkali metal alcoholates, etc. as the base component suffer from a problem that the β-ketoesters thus formed are liable to further undergo the secondary reaction and thus only a poor yield can be achieved.

When a magnesium alcoholate is employed as the improved base component, on the other hand, there arises a problem in safety, i.e., the evolution of explosive hydrogen gas in the process of the formation of the alcoholate from metallic magnesium and an alcohol.

When the above-mentioned process with the use of a calcium compound is applied to the production of 3-oxocarboxylic acid esters, only a poor yield can be achieved for the following reasons 1) and 2). In addition, this process brings about another problem of environmental pollution.

1) Aqueous ammonia, which is employed to promote the deacetylation of the intermediate formed from the 3-oxocarboxylic acid ester and acetoacetic ester, causes the formation of carboxylic acid amide crystals as the by-product. Thus the yield is lowered and the post-treatment becomes troublesome.

2) To activate the calcium compound, it is needed to use methylene chloride, i.e., a halogen compound which is likely to cause environmental pollution.

Further, the above-mentioned process with the use of magnesium enolate of an acetoacetic ester involves a troublesome procedure of adding a tertiary amine in the step of the acylation through the reaction with a carboxylic acid chloride. In the above-mentioned process with the use of a magnesium complex or a calcium complex, furthermore, the acylation reaction should be performed at a high temperature.

For these reasons, it has been urgently required to develop a process for producing β-oxocarboxylic acid esters which is economically advantageous and applicable to industrial production.

The present inventors have conducted extensive studies on a process for producing 3-oxocarboxylic acid esters which are useful as intermediates in the synthesis of ceramides to be used as a humectant, biodegradable polymers, drugs, etc. so as to solve the problems described above. As a result, they have successfully established a process which is economically advantageous and applicable to industrial production, thus completing the present invention.

SUMMARY OF THE INVENTION

Accordingly, the present invention is as follows.

1. A process for producing a 3-oxocarboxylic acid ester represented by the following general formula (I):

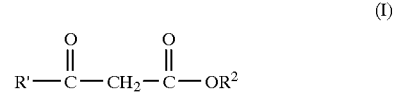

wherein $R^1$ represents a linear or branched alkyl group having 3 to 17 carbon atoms or an optionally substituted phenyl or benzyl group; and $R^2$ represents a linear or branched alkyl group having 1 to 4 carbon atoms; which comprises reacting an acetoacetic ester represented by the following general formula (II):

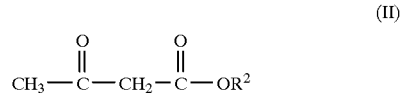

wherein $R^2$ represents a liner or branched alkyl group having 1 to 4 carbon atoms; with a calcium compound, a barium compound or a strontium compound in the presence of an organic solvent at a temperature of 10 to 120° C., further reacting the obtained product with a carboxylic acid chloride to thereby acylate it, and then adding thereto an alcohol in an amount 1 to 5 times by mol as much as the calcium compound, barium compound or strontium compound to thereby deacetylate the same.

2. A process for producing a 3-oxocarboxylic acid ester represented by the following general formula (I):

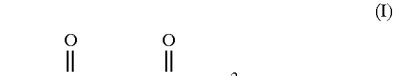

wherein $R^1$ represents a linear or branched alkyl group having 3 to 17 carbon atoms or an optionally substituted phenyl or benzyl group; and $R^2$ represents a linear or branched alkyl group having 1 to 4 carbon atoms; which comprises reacting an acetoacetic ester represented by the following general formula (II):

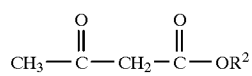

(II)

wherein R² represents a liner or branched alkyl group having 1 to 4 carbon atoms;
with calcium hydroxide in the presence of toluene at a temperature of 80 to 110° C., further reacting the obtained product with a carboxylic acid chloride to thereby acylate it, and then adding thereto an alcohol R²OH, wherein R² is the same as the above-mentioned one, in an amount 1 to 5 times by mol as much as the calcium hydroxide to thereby deacetylate the same.

DETAILED DESCRIPTION OF THE INVENTION

Now, the present invention will be described in greater detail.

The group $R^1$ as described above represents a linear or branched alkyl group having 3 to 17 carbon atoms or an optionally substituted phenyl or benzyl group. Examples thereof include n-propyl, isopropyl, n-butyl, sec-butyl, isobutyl, neobutyl, tert-butyl, n-pentyl, isopentyl, neopentyl, n-hexyl, 1-methylhexyl, n-heptyl, 1-ethylpentyl, n-octyl, n-nonyl, n-decyl, n-undecyl, n-dodecyl, n-tridecyl, n-tetradecyl, n-pentadecyl, n-hexadecyl, n-heptadecyl, phenyl, o-methoxyphenyl, m-methoxyphenyl, p-methoxyphenyl, p-ethylphenyl, p-isopropylphenyl, p-n-butylphenyl, p-tert-butylphenyl, o-chlorophenyl, m-chlorophenyl, p-chlorophenyl, o-bromophenyl, m-bromophenyl, p-bromophenyl, benzyl, o-methylbenzyl, m-methylbenzyl, p-methylbenzyl, o-methoxybenzyl, m-methoxybenzyl, p-methoxybenzyl, o-chlorobenzyl, m-chlorobenzyl, p-chlorobenzyl, o-bromobenzyl, m-bromobenzyl and p-bromobenzyl groups. In particular, higher alkyl groups having 8 to 17 carbon atoms and optionally substituted phenyl or benzyl groups are preferable therefor.

The group $R^2$ as described above represents a linear or branched alkyl group having 1 to 4 carbon atoms. Examples thereof include methyl, ethyl, n-propyl, isopropyl, n-butyl, isobutyl and tert-butyl groups.

As the organic solvent to be used in the step of the reaction between an acetoacetic ester and a calcium compound, a barium compound or a strontium compound, it is preferable to use an aromatic hydrocarbon organic solvent. As the aromatic hydrocarbon organic solvent, use can be made of benzene, toluene, xylene or the like. Among all, toluene is particularly preferable therefor. When a calcium compound is employed, the reaction is performed at a temperature of from 10 to 120° C., preferably from 80 to 110° C. When a barium compound or a strontium compound is employed, the reaction is performed at a temperature of from 10 to 40° C., preferably from 20 to 30° C.

Examples of the calcium compound, barium compound or strontium compound usable in the present invention include calcium oxide, calcium hydroxide, calcium sulfate, calcium carbonate, barium oxide, barium hydroxide, barium sulfate, barium carbonate, strontium oxide, strontium hydroxide, strontium sulfate and strontium carbonate. Among all, it is preferable to use calcium hydroxide therefor.

Examples of the carboxylic acid chloride usable in the present invention include palmitoyl chloride, octanoyl chloride, dodecanoyl chloride, butyryl chloride, pentadecanoyl chloride, and phenylacetyl chloride.

The calcium compound, barium compound or strontium compound is employed in an amount at least 0.5 to 1.5 times by mol as much as the carboxylic acid chloride. When the cost and the effects on the environment (waste water, etc.) are taken into consideration, it is preferable to use such a compound in an amount 0.6 to 1.3 times by mol as much. When its amount is less than 0.6 time by mol as much, the unreacted matters remain in a large amount. When it is employed in an excessive amount, i.e., 1.3 times by mol as much or more, on the other hand, there arises a problem of the formation of a by-product.

It is also possible that such a compound is used in the form of a metal chelate complex together with the acetoacetic ester.

The acetoacetic ester is employed in an amount at least 2 times by mol, preferably from 2 to 8 times by mol, as much as the carboxylic acid chloride.

In the present invention, the acetoacetic ester is acylated and then deacetylated by adding an alcohol thereto. As the alcohol for the deacetylation, use is made of one wherein $R^2$ has the same number of carbon atoms as the above-mentioned one, thus inhibiting the occurrence of side-reactions such as transesterification. The addition of this alcohol causes a great increase in the yield of the 3-oxocarboxylic acid ester, compared with the case where no alcohol is added.

The term "an alcohol $R^2OH$ wherein $R^2$ is the same as the one as used in the present invention" means methanol, ethanol or isopropanol when $R^2$ is a methyl, ethyl or isopropyl group respectively. This alcohol is employed in an amount 1 to 5 times by mol, preferably 1.5 to 3 times by mol, as much as the calcium compound, barium compound or strontium compound.

The deacetylation reaction is performed at a temperature of from 10 to 120° C., preferably from 80 to 110° C., when a calcium compound is used. When a barium compound or a strontium compound is used, it is performed at a temperature of from 10 to 40° C., preferably from 20 to 30° C. This reaction is completed within 10 to 20 hours.

The 3-oxocarboxylic acid ester thus formed is washed with the solvent together with dilute sulfuric acid to thereby remove therefrom the calcium compound, barium compound or strontium compound as a water-soluble or insoluble solid matter. Subsequently, the product can be highly purified through distillation or recrystallization.

According to the present invention, 3-oxocarboxylic acid esters, which are useful as intermediates in the synthesis of ceramides to be used as a humectant, biodegradable polymers, drugs, etc., can be produced at a high purity and a high yield. The present invention further makes it possible to produce the 3-oxocarboxylic acid esters while neither causing any problem in safety nor requiring any troublesome procedure such as post-treatment.

To further illustrate the present invention in greater detail, and not by way of limitation, the following examples will be given.

In these examples, physical data were determined by using the instruments and conditions as will be specified below.
1) Chemical purity
   Gas chromatograph: HP-5890 (Hewlett-Packard, Ltd.)
      column: Silicone NB-1 (0.25 mm×30 m) (GL Science, Ltd.)
      temperature: 100–220° C., elevated at 5° C./min.
   Liquid chromatograph: L-6200 (Hitachi, Ltd.)
      column: Inertsil ODS-2 (GL Science, Ltd.)
      solvent: acetonitrile/methanol/water=47.5/47.5/5
      flow rate: 1.0 ml/min
      detector: ultraviolet absorptiometer L-4000 (Hitachi, Ltd., 210 nm).
2) Proton nuclear magnetic resonance ($^1$H-NMR)
   AM-400 (400 MHz) (Bruker, Inc.)
      internal standard: tetramethylsilane.

EXAMPLE 1

Synthesis of methyl 3-oxooctadecanoate:

To 460 ml of toluene were added 76.9 g (0.662 mol) of methyl acetoacetate and 12.3 g (0.166 mol) of calcium hydroxide. The resulting mixture was heated and stirred at 80 to 110° C. for 2.5 hours under dehydration. After cooling the reaction mixture to 50 to 60° C., 70 g (0.255 mol) of palmitoyl chloride was dropped thereinto over 1.5 hours. The resulting mixture was stirred as such for 18 hours without heating. Next, 29 g (0.906 mol) of methanol was added thereto and the mixture was heated and stirred at 60 to 80° C. for 4 hours.

After cooling the reaction mixture, 18 g of conc. hydrochloric acid was added thereto. Then it was separated out and the organic layer was washed successively with 250 ml of water, 100 ml of a 2% aqueous solution of sodium carbonate and a 5% aqueous solution of sodium chloride. After distilling off the toluene under reduced pressure, the residue was dissolved in 700 ml of methanol and allowed to stand at −20° C. overnight. The crystals thus precipitated were filtered and dried to thereby give 61.8 g of methyl 3-oxooctadecanoate as white crystals (m.p.: 40–41° C., LC purity: 98%) at a yield of 78%.

The physical data of this product are as follows.

$^1$H-NMR (CDCl$_3$, δ ppm): 0.81 (3H, t, J=7 Hz), 1.18 (24H, m), 1.50–1.54 (2H, m), 2.46 (2H, t, J=7 Hz), 3.37 (2H, s), 3.66 (3H, s).

COMPARATIVE EXAMPLE 1

Synthesis of methyl 3-oxooctadecanoate:

Synthesis was performed in accordance with the reaction described in Japanese Patent No. 2518769.

77.8 g (1.05 mol) of calcium hydroxide was added to 550 ml of methylene chloride. 116 g (1.0 mol) of methyl acetoacetate was dropped thereinto at 20 to 30° C. under vigorously stirring over 20 minutes. Then stirring was continued for 30 minutes.

Next, 288 g (1.05 mol) of palmitoyl chloride was dropped into the solution obtained above at 25 to 35° C. over 1 hour. Subsequently, stirring was continued for 2 hours at 30 to 35° C. Then a solution of 56.2 g (1.05 mol) of ammonium chloride dissolved in 350 ml of water was added to the reaction mixture and the obtained mixture was stirred at 30° C. for 30 minutes.

After adjusting the pH value to 9.0 by adding aqueous ammonia, the mixture was stirred at 30 to 35° C. for 3 hours.

Then conc. hydrochloric acid was added to the reaction mixture so as to regulate the pH value to 1. After separating out, the organic layer was washed with a 5% aqueous solution of sodium hydrogencarbonate and water. After distilling off the methylene chloride, 200 ml of toluene was added to the residue and the mixture was stirred under cooling. The palmitamide thus formed as the by-product was filtered off and toluene was distilled off from the mother liquor under reduced pressure. Then the residue was dissolved in 700 ml of methanol and allowed to stand at −20° C. overnight. The crystals thus precipitated were filtered and dried to thereby give 120.7 g of methyl 3-oxooctadecanoate as white crystals (LC purity: 93%) at a yield of 37% on the basis of the palmitoyl chloride.

EXAMPLES 2 TO 4

Synthesis of methyl 3-oxooctadecanoate:

The procedure of EXAMPLE 1 was repeated but varying the amounts of methyl acetoacetate and calcium hydroxide. TABLE 1 summarizes the results.

COMPARATIVE EXAMPLE 2

Synthesis of methyl 3-oxooctadecanoate:

The procedure of EXAMPLE 1 was repeated but adding no methanol to the reaction mixture. TABLE 1 also shows the result.

TABLE 1

|  | Methyl acetoacetate (molar ratio) | Base | Base (molar ratio) | Addition of methanol | Methyl 3-oxooctadecanoate (g) | Yield (%) |
| --- | --- | --- | --- | --- | --- | --- |
| Ex. 2 | 2.0 | Ca(OH)$_2$ | 0.65 | yes | 59.4 | 75 |
| Ex. 3 | 6.0 | Ca(OH)$_2$ | 0.65 | yes | 53.9 | 68 |
| Ex. 4 | 8.0 | Ca(OH)$_2$ | 0.65 | yes | 53.1 | 67 |
| Comp. Ex. 2 | 2.0 | Ca(OH)$_2$ | 0.65 | no | 34.9 | 44 |

EXAMPLE 5

Synthesis of methyl 3-oxooctadecanaote:

To 90 ml of toluene was added 18.2 g (purity: 90%, 0.107 mol) of barium oxide. After adding 0.23 ml of water and activating under vigorously stirring, 42.3 g (0.364 mol) of methyl acetoacetate was dropped thereinto at 20 to 30° C. over 1 hour. Then stirring was continued for 1 hour.

Into the obtained solution was dropped 25 g (0.091 mol) of palmitoyl chloride at 20 to 30° C. over 1 hour and stirring was continued for additional 1 hour. Next, 6.8 g (0.213 mol) of methanol was added to the reaction mixture which was then stirred for 16 hours and for additional 40 minutes at 40° C.

After adjusting the pH value of the reaction mixture to 1 by adding dilute sulfuric acid, the insoluble barium salt was filtered off. After separating out, the toluene layer was washed with a 5% aqueous solution of sodium hydrogencarbonate and a 5% aqueous solution of sodium chloride. After distilling off the toluene under reduced pressure, the residue was dissolved in 700 ml of methanol and allowed to stand at −20° C. overnight. The crystals thus precipitated were filtered and dried to thereby give 21.1 g of methyl 3-oxooctadecanoate as white crystals (m.p.: 36–38° C., LC purity: 92.8%) at a yield of 74%.

EXAMPLE 6
Synthesis of ethyl 3-oxooctadecanoate:

To 300 ml of toluene were added 50 g (0.384 mol) of ethyl acetoacetate and 7.11 g (0.096 mol) of calcium hydroxide. The resulting mixture was heated and stirred at 80 to 110° C. for 2.5 hours under dehydration. After cooling the reaction mixture to 50 to 60° C., 40.6 g (0.148 mol) of palmitoyl chloride was dropped thereinto over 1.5 hours. The resulting mixture was stirred as such for 18 hours without heating. Next, 24.5 g (0.533 mol) of ethanol was added thereto and the mixture was heated and stirred at 60 to 80° C. for 4 hours.

After cooling the reaction mixture, 18.9 g of conc. hydrochloric acid was added thereto. Then it was separated out and the organic layer was washed successively with 160 ml of water, 70 ml of a 2% aqueous solution of sodium carbonate and a 5% aqueous solution of sodium chloride. After distilling off the toluene under reduced pressure, the residue was dissolved in 500 ml of methanol and allowed to stand at −20° C. overnight. The crystals thus precipitated were filtered and dried to thereby give 30.2 g of ethyl 3-oxooctadecanoate as white crystals (m.p.: 37–38° C., LC purity: 96%) at a yield of 68%.

EXAMPLE 7
Synthesis of methyl 3-oxodecanoate:

To 300 ml of toluene were added 50 g (0.431 mol) of methyl acetoacetate and 7.97 g (0.108 mol) of calcium hydroxide. The resulting mixture was heated and stirred at 80 to 110° C. for 2.5 hours under dehydration. After cooling the reaction mixture to 50 to 60° C., 26.9 g (0.165 mol) of octanoyl chloride was dropped thereinto over 1.5 hours. The resulting mixture was stirred as such for 18 hours without heating. Next, 19.1 g (0.597 mol) of methanol was added thereto and the mixture was heated and stirred at 60 to 80° C. for 4 hours.

After cooling the reaction mixture, 33.6 g of conc. hydrochloric acid was added thereto. Then it was separated out and the organic layer was washed successively with 160 ml of water, 70 ml of a 2% aqueous solution of sodium carbonate and a 5% aqueous solution of sodium chloride. After distilling off the toluene under reduced pressure, 45.3 g of an oily product was obtained. 8.8 g of the methyl acetoacetate was recovered by distillation under reduced pressure. Then 28.9 g of methyl 3-oxodecanoate was obtained (b.p.: 72–75° C./0.1 mmHg, GC purity: 89%) at a yield of 78%.

The physical data of this product are as follows.

$^1$H-NMR (CDCl$_3$, δ ppm): 0.88 (3H, t, J=7.1 Hz), 1.26–1.32 (16H, m), 1.57–1.61 (2H, m), 2.53 (2H, t, J=7.1 Hz), 3.45 (2H, s), 3.74 (3H, s).

EXAMPLE 8
Synthesis of methyl 3-oxotetradecanoate:

To 300 ml of toluene were added 50 g (0.431 mol) of methyl acetoacetate and 7.97 g (0.108 mol) of calcium hydroxide. The resulting mixture was heated and stirred at 80 to 110° C. for 2.5 hours under dehydration. After cooling the reaction mixture to 50 to 60° C., 36.2 g (0.165 mol) of dodecanoyl chloride was dropped thereinto over 1.5 hours. The resulting mixture was stirred as such for 18 hours without heating. Next, 19.1 g (0.597 mol) of methanol was added thereto and the mixture was heated and stirred at 60 to 80° C. for 4 hours.

After cooling the reaction mixture, 33.6 g of conc. hydrochloric acid was added thereto. Then it was separated out and the organic layer was washed successively with 160 ml of water, 70 ml of a 2% aqueous solution of sodium carbonate and a 5% aqueous solution of sodium chloride. After distilling off the toluene under reduced pressure, the residue was dissolved in 200 ml of methanol and allowed to stand at −20° C. overnight. The crystals thus precipitated were filtered and dried to thereby give 30.1 g of methyl 3-oxotetradecanoate as white crystals (137–139° C./1 mmHg, m.p.: 29° C., GC purity: 94%) at a yield of 68%.

The physical data of this product are as follows.

$^1$H-NMR (CDCl$_3$, δ ppm): 0.88 (3H, t, J=7 Hz), 1.28 (17H, m), 1.55–1.59 (2H, m), 2.53 (2H, t, J 7 Hz), 3.45 (2H, s), 3.74 (3H, s).

EXAMPLE 9
Synthesis of methyl 3-oxohexanoate:

To 360 ml of toluene were added 50 g (0.431 mol) of methyl acetoacetate and 7.79 g (0.108 mol) of calcium hydroxide. The resulting mixture was heated and stirred at 80 to 110° C. for 2.5 hours under dehydration. After cooling the reaction mixture, 17.6 g (0.166 mol) of n-butyryl chloride was dropped thereinto over 1.5 hours. The resulting mixture was stirred as such for 18 hours without heating. Next, 19.1 g (0.597 mol) of methanol was added thereto and the mixture was heated and stirred at 60 to 80° C. for 4 hours.

After cooling the reaction mixture, 33.6 g of conc. hydrochloric acid was added thereto. Then it was separated out and the organic layer was washed successively with 160 ml of water, 70 ml of a 2% aqueous solution of sodium carbonate and a 5% aqueous solution of sodium chloride. After distilling off the toluene under reduced pressure, 29.4 g of an oily product was obtained.

8.9 g of the methyl acetoacetate was recovered by distillation under reduced pressure. Then 18.1 g of methyl 3-oxohexanoate was obtained (b.p.: 80–86° C./15 mmHg, GC purity: 87%) at a yield of 67%.

The physical data of this product are as follows.

$^1$H-NMR (CDCl$_3$, δ ppm): 0.93 (3H, t, J=7.4 Hz), 1.61–1.66 (2H, m), 2.52 (2H, t, J=7.4 Hz), 3.45 (2H, s), 3.74 (3H, s).

EXAMPLE 10
Synthesis of methyl 3-oxoheptadecanoate:

To 360 ml of toluene were added 50 g (0.431 mol) of methyl acetoacetate and 7.79 g (0.108 mol) of calcium hydroxide. The resulting mixture was heated and stirred at 80 to 110° C. for 2.5 hours under dehydration. After cooling the reaction mixture to 50 to 60° C., 43.2 g (0.166 mol) of pentadecanoyl chloride was dropped thereinto over 1.5 hours. The resulting mixture was stirred as such for 18 hours without heating. Next, 19.1 g (0.597 mol) of methanol was added thereto and the mixture was heated and stirred at 60 to 80° C. for 4 hours.

After cooling the reaction mixture, 33.6 g of conc. hydrochloric acid was added thereto. Then it was separated out and the organic layer was washed successively with 160 ml of water, 70 ml of a 2% aqueous solution of sodium carbonate and a 5% aqueous solution of sodium chloride. After distilling off the toluene under reduced pressure, the residue was dissolved in 200 ml of methanol and allowed to stand at −20° C. overnight. The crystals thus precipitated were filtered and dried to thereby give 32.4 g of methyl 3-oxoheptadecanoate as white crystals (m.p.: 51–53° C., LC purity: 93%) at a yield of 61%.

The physical data of this product are as follows.

$^1$H-NMR (CDCl$_3$, δ ppm): 0.88 (3H, t, J=7 Hz), 1.26–1.30 (28H, m), 1.57–1.60 (2H, m), 2.53 (2H, t, J=7 Hz), 3.44 (2H, s), 3.74 (3H, s).

EXAMPLE 11
Synthesis of methyl 4-phenyl-3-oxobutanoate:

To 200 ml of toluene was added 40.0 g (purity: 90%, 0.235 mol) of barium oxide. After adding 0.5 ml of water and activating under vigorously stirring, 92.9 g (0.8 mol) of methyl acetoacetate was dropped thereinto at 20 to 30° C. over 1 hour. Then stirring was continued for 1 hour.

Into the obtained solution was dropped 30.9 g (0.2 mol) of phenylacetyl chloride at 20 to 30° C. over 1 hour and stirring was continued for additional 1 hour. Next, 15.0 g (0.47 mol) of methanol was added to the reaction mixture which was then stirred for 16 hours.

After adjusting the pH value of the reaction mixture to 1 by adding dilute sulfuric acid, the insoluble barium salt was filtered off. After separating out, the toluene layer was washed with a 5% aqueous solution of sodium hydrogencarbonate and a 5% aqueous solution of sodium chloride. After distilling off the toluene under reduced pressure, 86.6 g of an oily product was obtained.

45.7 g of the methyl acetoacetate was recovered by distillation under reduced pressure. Then 29.5 g of methyl 4-phenyl-3-oxobutanoate was obtained (b.p.: 122–127° C./0.6 mmHg, GC purity: 90%) at a yield of 69%.

The physical data of this product are as follows.

$^1$H-NMR (CDCl$_3$, δ ppm): 3.45 (2H, s), 3.70 (3H, s), 3.82 (2H, s), 7.19–7.36 (5H, m).

COMPARATIVE EXAMPLE 3
Synthesis of methyl 4-phenyl-3-oxobutanoate:

Synthesis was performed in accordance with the reaction described in Japanese Patent No. 2518769.

77.8 g (1.05 mol) of calcium hydroxide was added to 550 ml of methylene chloride. 116 g (1.0 mol) of methyl acetoacetate was dropped thereinto at 20 to 30° C. under vigorously stirring over 20 minutes. Then stirring was continued for 30 minutes.

Next, 162.3 g (1.05 mol) of phenylacetyl chloride was dropped into the solution obtained above at 25 to 35° C. over 1 hour. Subsequently, stirring was continued for 2 hours at 30 to 35° C. Then a solution of 56.2 g (1.05 mol) of ammonium chloride dissolved in 350 ml of water was added to the reaction mixture and the obtained mixture was stirred at 30° C. for 30 minutes.

After adjusting the pH value to 9.0 by adding aqueous ammonia, the mixture was stirred at 30 to 35° C. for 3 hours. Then conc. hydrochloric acid was added to the reaction mixture so as to regulate the pH value to 1. After separating out, the organic layer was washed with a 5% aqueous solution of sodium hydrogencarbonate and water. After distilling off the methylene chloride, 200 ml of toluene was added to the residue and the mixture was stirred under cooling. The phenylacetamide thus formed as the by-product was filtered off at −10° C. and toluene was distilled off from the mother liquor.

17.3 g of the methyl acetoacetate was recovered by distillation under reduced pressure. Then 105.6 g of methyl 4-phenyl-3-oxobutanoate was obtained (GC purity: 91%) at a yield of 48% on the basis of the phenylacetyl chloride. Synthesis of methyl 4-phenyl-3-oxobutanoate:

EXAMPLES 12 TO 14
Synthesis of methyl 4-phenyl-3-oxobutanoate:

The procedure of EXAMPLE 11 was repeated but varying the molar ratio of methyl acetoacetate. TABLE 2 summarizes the results.

COMPARATIVE EXAMPLE 4
Synthesis of methyl 4-phenyl-3-oxobutanoate:

The procedure of EXAMPLE 11 was repeated but adding no methanol to the reaction mixture. TABLE 2 also shows the result.

TABLE 2

|  | Methyl acetoacetate (molar ratio) | Base | Base (molar ratio) | Addition of methanol | Methyl 3-oxo-octadecanoate (g) | Yield (%) |
| --- | --- | --- | --- | --- | --- | --- |
| Ex. 12 | 2.0 | BaO | 1.17 | yes | 24.9 | 58 |
| Ex. 13 | 6.0 | BaO | 1.17 | yes | 27.3 | 66 |
| Ex. 14 | 8.0 | BaO | 1.17 | yes | 27.9 | 66 |
| Comp. Ex. 4 | 2.0 | BaO | 1.17 | no | 20.8 | 48 |

EXAMPLE 15

To 200 ml of toluene was added 35.80 g of barium oxide. After adding 0.5 ml of water and activating under vigorously stirring, 92.9 g (0.8 mol) of methyl acetoacetate was dropped thereinto at 20 to 30° C. over 1 hour. Then stirring was continued for 1 hour.

Into the obtained solution was dropped 28.1 g (0.2 mol) of phenylacetyl chloride at 20 to 30° C. over 1 hour and stirring was continued for additional 1 hour. Next, 13.5 g (0.42 mol) of methanol was added to the reaction mixture which was then stirred for 16 hours.

After adjusting the pH value of the reaction mixture to 1 by adding dilute sulfuric acid, the insoluble barium salt was filtered off. After separating out, the toluene layer was washed with a 5% aqueous solution of sodium hydrogencarbonate and a 5% aqueous solution of sodium chloride. After distilling off the toluene under reduced pressure, 72.4 g of an oily product was obtained.

19.9 g of the methyl acetoacetate was recovered by distillation under reduced pressure. Then 32.2 g of methyl 4-phenyl-3-oxopropanoate was obtained (b.p.: 96–97° C./0.6 mmHg, GC purity: 92.6%) at a yield of 84%.

The physical data of this product are as follows.

$^1$H-NMR (CDCl$_3$, δ ppm): 3.74 (3H, s), 4.01 (2H, s), 7.41–7.79 (3H, m), 7.93–7.96 (2H, m).

EXAMPLE 16
Synthesis of ethyl 4-phenyl-3-oxobutanoate:

To 200 ml of toluene was added 40.0 g of barium oxide (purity: 90%, 0.235 mol). After adding 0.5 ml of water and activating under vigorously stirring, 104.1 g (0.8 mol) of ethyl acetoacetate was dropped thereinto at 20 to 30° C. over 1 hour. Then stirring was continued for 1 hour.

Into the obtained solution was dropped 30.9 g (0.2 mol) of phenylacetyl chloride at 20 to 30° C. over 1 hour and stirring was continued for additional 1 hour. Next, 21.7 g (0.47 mol) of ethanol was added to the reaction mixture which was then stirred for 16 hours.

After adjusting the pH value of the reaction mixture to 1 by adding dilute sulfuric acid, the insoluble barium salt was filtered off. After separating out, the toluene layer was washed with a 5% aqueous solution of sodium hydrogencarbonate and a 5% aqueous solution of sodium chloride. After distilling off the toluene under reduced pressure, 95.7 g of an oily product was obtained.

48.1 g of the ethyl acetoacetate was recovered by distillation under reduced pressure. Then 30.9 g of ethyl 4-phenyl-3-oxobutanoate was obtained (b.p.: 125–130° C./0.6 mmHg, GC purity: 88%) at a yield of 66%.

The physical data of this product are as follows.

$^1$H-NMR (CDCl$_3$, δ ppm): 1.24 (3H, t, J=7.1 Hz), 3.44 (2H, s), 3.82 (2H, s), 4.16 (2H, q, J=7.1 Hz), 7.20–7.35 (5H, m).

EXAMPLE 17
Synthesis of tert-butyl 4-phenyl-3-oxobutanoate:

To 150 ml of toluene was added 29.9 g of barium oxide (purity: 90%, 0.176 mol). After adding 0.5 ml of water and activating under vigorously stirring, 94.7 g (0.6 mol) of tert-butyl acetoacetate was dropped thereinto at 20 to 30° C. over 1 hour. Then stirring was continued for 1 hour.

Into the obtained solution was dropped 23.2 g (0.15 mol) of phenylacetyl chloride at 20 to 30° C. over 1 hour and stirring was continued for additional 1 hour. Next, 26.1 g (0.35 mol) of tert-butanol was added to the reaction mixture which was then stirred for 16 hours.

After adjusting the pH value of the reaction mixture to 1 by adding dilute sulfuric acid, the insoluble barium salt was filtered off. After separating out, the toluene layer was washed with a 5% aqueous solution of sodium hydrogencarbonate and a 5% aqueous solution of sodium chloride. After distilling off the toluene under reduced pressure, 105.6 g of an oily product was obtained.

54.0 g of the tert-butyl acetoacetate was recovered by distillation under reduced pressure. Then 25.1 g of tert-butyl 4-phenyl-3-oxobutanoate was obtained (b.p.: 128–132° C./0.5 mmHg, GC purity: 91%) at a yield of 65%.

The physical data of this product are as follows.

$^1$H-NMR (CDCl$_3$, δ ppm): 1.46 (9H, s), 3.36 (2H, s), 3.81 (2H, s), 7.20–7.36 (5H, m).

EXAMPLE 18
Synthesis of methyl 4-phenyl-3-oxobutanoate:

To 200 ml of toluene was added 24.2 g (0.235 mol) of strontium oxide. After adding 0.5 ml of water and activating under vigorously stirring, 92.9 g (0.8 mol) of methyl acetoacetate was dropped thereinto at 20 to 30° C. over 1 hour. Then stirring was continued for 1 hour.

Into the obtained solution was dropped 30.9 g (0.2 mol) of phenylacetyl chloride at 20 to 30° C. over 1 hour and stirring was continued for additional 1 hour. Next, 15.0 g (0.47 mol) of methanol was added to the reaction mixture which was then stirred for 16 hours.

After adjusting the pH value of the reaction mixture to 1 by adding dilute sulfuric acid, the insoluble strontium salt was filtered off. After separating out, the toluene layer was washed with a 5% aqueous solution of sodium hydrogencarbonate and a 5% aqueous solution of sodium chloride. After distilling off the toluene under reduced pressure, 83.1 g of an oily product was obtained.

47.2 g of the methyl acetoacetate was recovered by distillation under reduced pressure. Then 28.0 g of methyl 4-phenyl-3-oxobutanoate was obtained (GC purity: 95%) at a yield of 69%.

EXAMPLE 19
Synthesis of methyl 4-phenyl-3-oxobutanoate:

To 200 ml of toluene was added 74.1 g (0.235 mol) of barium hydroxide octahydrate. Under vigorously stirring, 92.9 g (0.8 mol) of methyl acetoacetate was dropped thereinto at 20 to 30° C. over 1 hour. Then stirring was continued for 1 hour.

Into the obtained solution was dropped 30.9 g (0.2 mol) of phenylacetyl chloride at 20 to 30° C. over 1 hour and stirring was continued for additional 1 hour. Next, 15.0 g (0.47 mol) of methanol was added to the reaction mixture which was then stirred for 16 hours.

After adjusting the pH value of the reaction mixture to 1 by adding dilute sulfuric acid, the insoluble barium salt was filtered off. After separating out, the toluene layer was washed with a 5% aqueous solution of sodium hydrogencarbonate and a 5% aqueous solution of sodium chloride. After distilling off the toluene under reduced pressure, 84.5 g of an oily product was obtained.

48.4 g of the methyl acetoacetate was recovered by distillation under reduced pressure. Then 23.4 g of methyl 4-phenyl-3-oxobutanoate was obtained (GC purity: 92%) at a yield of 56%.

EXAMPLE 20
Synthesis of methyl 4-phenyl-3-oxobutanoate:

To 200 ml of toluene was added 62.5 g (0.235 mol) of strontium hydroxide octahydrate. Under vigorously stirring, 92.9 g (0.8 mol) of methyl acetoacetate was dropped thereinto at 20 to 30° C. over 1 hour. Then stirring was continued for 1 hour.

Into the obtained solution was dropped 30.9 g (0.2 mol) of phenylacetyl chloride at 20 to 30° C. over 1 hour and stirring was continued for additional 1 hour. Next, 15.0 g (0.47 mol) of methanol was added to the reaction mixture which was then stirred for 16 hours.

After adjusting the pH value of the reaction mixture to 1 by adding dilute sulfuric acid, the insoluble strontium salt was filtered off. After separating out, the toluene layer was washed with a 5% aqueous solution of sodium hydrogencarbonate and a 5% aqueous solution of sodium chloride. After distilling off the toluene under reduced pressure, 85.1 g of an oily product was obtained.

43.5 g of the methyl acetoacetate was recovered by distillation under reduced pressure. Then 23.4 g of methyl 4-phenyl-3-oxobutanoate was obtained (GC purity: 90%) at a yield of 55%.

While the invention has been described in detail and with reference to specific embodiments thereof, it will be apparent to one skilled in the art that various changes and modifications can be made therein without departing from the spirit and scope thereof.

What is claimed is:

1. A process for producing a 3-oxocarboxylic acid ester represented by the following general formula (I):

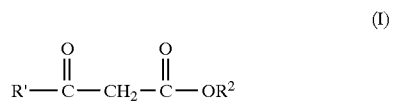

wherein $R^1$ represents a linear or branched alkyl group having 3 to 17 carbon atoms or an optionally substituted phenyl or benzyl group; and $R^2$ represents a linear or branched alkyl group having 1 to 4 carbon atoms; which comprises reacting an acetoacetic ester represented by the following general formula (II):

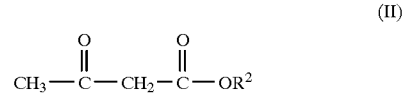

wherein $R^2$ represents a liner or branched alkyl group having 1 to 4 carbon atoms;
with a calcium compound, a barium compound or a strontium compound in the presence of an organic solvent at a temperature of 10 to 120° C., further reacting the obtained product with a carboxylic acid chloride to thereby acylate it, and then adding thereto an alcohol in an amount 1 to 5 times by mol as much as the calcium compound, barium compound or strontium compound to thereby deacetylate the same.

2. A process for producing a 3-oxocarboxylic acid ester represented by the following general formula (I):

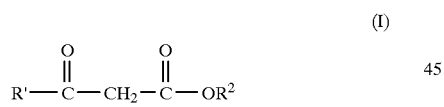

wherein $R^1$ represents a linear or branched alkyl group having 3 to 17 carbon atoms or an optionally substituted phenyl or benzyl group; and $R^2$ represents a linear or branched alkyl group having 1 to 4 carbon atoms; which comprises reacting an acetoacetic ester represented by the following general formula (II):

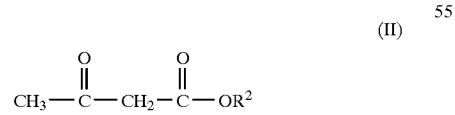

wherein $R^2$ represents a liner or branched alkyl group having 1 to 4 carbon atoms;
with calcium hydroxide in the presence of toluene at a temperature of 80 to 110° C., further reacting the obtained product with a carboxylic acid chloride to thereby acylate it, and then adding thereto an alcohol $R^2OH$, wherein $R^2$ is the same as the above-mentioned one, in an amount 1 to 5 times by mol as much as the calcium hydroxide to thereby deacetylate the same.

3. The process for producing a 3-oxocarboxylic acid ester as claimed in claim 1, wherein said organic solvent is selected from the group consisting of benzene, toluene and xylene.

4. The process for producing a 3-oxocarboxylic acid ester as claimed in claim 1, wherein the first reaction is performed at a temperature of from 10 to 120° C. when a calcium compound is employed and from 10 to 40° C. when a barium compound or a strontium compound is employed.

5. The process for producing a 3-oxocarboxylic acid ester as claimed in claim 1, wherein the calcium compound, barium compound or strontium compound is selected from the group consisting of calcium oxide, calcium hydroxide, calcium sulfate, calcium carbonate, barium oxide, barium hydroxide, barium sulfate, barium carbonate, strontium oxide, strontium hydroxide, strontium sulfate and strontium carbonate.

6. The process for producing a 3-oxocarboxylic acid ester as claimed in claim 1, wherein the carboxylic acid chloride is selected from the group consisting of palmitoyl chloride, octanoyl chloride, dodecanoyl chloride, butyryl chloride, pentadecanoyl chloride, and phenylacetyl chloride.

7. A process for producing a 3-oxocarboxylic acid ester represented by the following general formula (I):

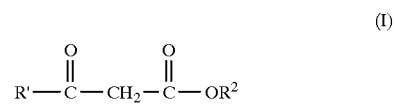

wherein $R^1$ represents a linear or branched alkyl group having 3 to 17 carbon atoms or an optionally substituted phenyl or benzyl group; and $R^2$ represents a linear or branched alkyl group having 1 to 4 carbon atoms;
which comprises reacting an acetoacetic ester represented by the following general formula (II):

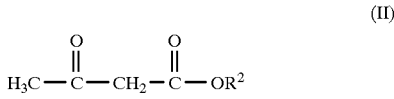

wherein $R^2$ represents a linear or branched alkyl group having 1 to 4 carbon atoms;
with a barium compound or a strontium compound in the presence of an organic solvent at a temperature of 10 to 120° C., further reacting the obtained product with a carboxylic acid chloride to thereby acylate it, and then adding thereto an alcohol in an amount 1 to 5 times by mol as much as the barium compound or strontium compound to thereby deacetylate the same.

8. A process for producing a 3-oxocarboxylic acid ester represented by the following general formula (I):

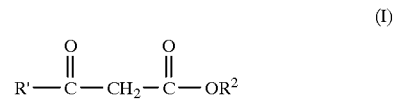

wherein $R^1$ represents a linear or branched alkyl group having 3 to 17 carbon atoms or an optionally substituted phenyl group; and $R^2$ represents a linear or branched alkyl group having 1 to 4 carbon atoms;

which comprises reacting an acetoacetic ester represented by the following general formula (II):

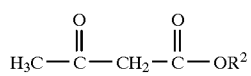 (II)

wherein $R^2$ represents a linear or branched alkyl group having 1 to 4 carbon atoms;

with barium hydroxide or strontium hydroxide in the presence of toluene at a temperature of 80 to 110° C., further reacting the obtained product with a carboxylic acid chloride to thereby acylate the obtained product, and then adding thereto an alcohol of the formula $R^2OH$, wherein $R^2$ is as defined above, in an amount of 1 to 5 times by mol as much as the barium hydroxide or strontium hydroxide to thereby deacetylate the same.

9. The process for producing a 3-oxocarboxylic acid ester as claimed in claim 7, wherein the first reaction is performed at a temperature of from 10 to 40° C.

10. The process for producing a 3-oxocarboxylic acid ester as claimed in claim 7, wherein the barium compound or strontium compound is selected from the group consisting of barium oxide, barium hydroxide, barium sulfate, barium carbonate, strontium oxide, strontium hydroxide, strontium sulfate and strontium carbonate.

11. The process for producing a 3-oxocarboxylic acid ester as claimed in claim 7, wherein the carboxylic acid chloride is selected from the group consisting of palmitoyl chloride, octanoyl chloride, dodecanoyl chloride, pentadecanoyl chloride, and phenylacetyl chloride.

* * * * *